United States Patent

(12) United States Patent  
Sugimoto

(10) Patent No.: US 8,945,211 B2  
(45) Date of Patent: Feb. 3, 2015

(54) TISSUE PLICATION DEVICE AND METHOD FOR ITS USE

(75) Inventor: Hiroatsu Sugimoto, Cambridge, MA (US)

(73) Assignee: Mitralign, Inc., Tewksbury, MA (US)

(*) Notice: Subject to any disclaimer, the term of this patent is extended or adjusted under 35 U.S.C. 154(b) by 769 days.

(21) Appl. No.: 12/557,655

(22) Filed: Sep. 11, 2009

(65) Prior Publication Data

US 2010/0070028 A1 Mar. 18, 2010

Related U.S. Application Data

(60) Provisional application No. 61/194,671, filed on Sep. 12, 2008.

(51) Int. Cl.  
*A61F 2/24* (2006.01)  
*A61B 17/00* (2006.01)  
*A61B 17/04* (2006.01)

(52) U.S. Cl.  
CPC .......... *A61F 2/2445* (2013.01); *A61B 17/00234* (2013.01); *A61B 17/0401* (2013.01); *A61B 2017/00243* (2013.01); *A61B 2017/00783* (2013.01); *A61B 2017/0414* (2013.01); *A61B 2017/0417* (2013.01); *A61B 2017/0464* (2013.01); *A61B 2017/0496* (2013.01)  
USPC ........................................ 623/2.37; 623/2.36

(58) Field of Classification Search  
USPC ................................. 623/2.36, 2.37  
See application file for complete search history.

(56) References Cited

U.S. PATENT DOCUMENTS

| | | | |
|---|---|---|---|
| 3,959,960 A | 6/1976 | Santos | |
| 3,995,619 A | 12/1976 | Glatzer | |
| 4,532,926 A * | 8/1985 | O—Holla | 606/220 |
| 5,171,259 A | 12/1992 | Inoue | |
| 5,192,302 A | 3/1993 | Kensey et al. | |
| 5,201,880 A | 4/1993 | Wright et al. | |
| 5,304,190 A | 4/1994 | Reckelhoff et al. | |
| 5,306,296 A * | 4/1994 | Wright et al. | 623/2.37 |
| 5,364,365 A | 11/1994 | Wortrich | |
| 5,450,860 A * | 9/1995 | O—Connor | 128/898 |
| 5,452,513 A | 9/1995 | Zinnbauer et al. | |
| 5,545,178 A * | 8/1996 | Kensey et al. | 606/213 |
| 5,674,279 A | 10/1997 | Wright et al. | |
| 5,879,366 A | 3/1999 | Shaw | |
| 5,944,738 A | 8/1999 | Amplatz et al. | |
| 6,027,514 A | 2/2000 | Stine et al. | |
| 6,113,611 A | 9/2000 | Allen et al. | |
| 6,589,208 B2 | 7/2003 | Ewers et al. | |
| 6,626,899 B2 | 9/2003 | Houser et al. | |
| 6,629,534 B1 | 10/2003 | St. Goar et al. | |
| 6,702,826 B2 * | 3/2004 | Liddicoat et al. | 606/151 |
| 6,964,683 B2 | 11/2005 | Kowalsky et al. | |
| 6,976,995 B2 | 12/2005 | Mathis et al. | |
| 7,004,958 B2 | 2/2006 | Adams et al. | |

(Continued)

FOREIGN PATENT DOCUMENTS

WO WO 2004/037317 5/2004  
WO WO 2005058239 6/2005

(Continued)

*Primary Examiner* — David Isabella  
*Assistant Examiner* — Jacqueline Woznicki  
(74) *Attorney, Agent, or Firm* — Leason Ellis LLP

(57) ABSTRACT

A device for treating mitral regurgitation including an anchor which features one or more reinforcing bars, ribbon and suture.

8 Claims, 2 Drawing Sheets

(56) References Cited

U.S. PATENT DOCUMENTS

| | | | |
|---|---|---|---|
| 7,115,110 B2 | 10/2006 | Frazier et al. | |
| 7,247,134 B2 | 7/2007 | Vidlund et al. | |
| 7,485,142 B2* | 2/2009 | Milo | 623/2.11 |
| 7,731,732 B2 | 6/2010 | Ken | |
| 7,749,250 B2 | 7/2010 | Stone et al. | |
| 7,771,455 B2 | 8/2010 | Ken | |
| 7,883,538 B2 | 2/2011 | To et al. | |
| 7,931,580 B2 | 4/2011 | Gertner et al. | |
| 8,172,871 B2 | 5/2012 | Ken | |
| 2001/0049492 A1 | 12/2001 | Frazier et al. | |
| 2002/0019649 A1 | 2/2002 | Sikora et al. | |
| 2002/0087169 A1 | 7/2002 | Brock et al. | |
| 2002/0128708 A1* | 9/2002 | Northrup et al. | 623/2.37 |
| 2003/0130731 A1* | 7/2003 | Vidlund et al. | 623/2.37 |
| 2003/0204205 A1 | 10/2003 | Sauer et al. | |
| 2003/0220685 A1* | 11/2003 | Hlavka et al. | 623/2.11 |
| 2004/0019378 A1* | 1/2004 | Hlavka et al. | 623/2.11 |
| 2004/0049211 A1 | 3/2004 | Tremulis et al. | |
| 2004/0097865 A1 | 5/2004 | Anderson et al. | |
| 2004/0122456 A1 | 6/2004 | Saadat et al. | |
| 2004/0127983 A1 | 7/2004 | Mortier et al. | |
| 2004/0186566 A1 | 9/2004 | Hindichs et al. | |
| 2004/0236419 A1* | 11/2004 | Milo | 623/2.36 |
| 2004/0243153 A1* | 12/2004 | Liddicoat et al. | 606/151 |
| 2005/0049634 A1 | 3/2005 | Chopra | |
| 2005/0065550 A1 | 3/2005 | Starksen et al. | |
| 2005/0107810 A1 | 5/2005 | Morales et al. | |
| 2005/0125011 A1 | 6/2005 | Spence et al. | |
| 2005/0197693 A1 | 9/2005 | Pai et al. | |
| 2005/0234481 A1 | 10/2005 | Waller | |
| 2005/0251208 A1 | 11/2005 | Elmer et al. | |
| 2005/0267533 A1 | 12/2005 | Gertner | |
| 2005/0283192 A1 | 12/2005 | Torrie et al. | |
| 2005/0288694 A1 | 12/2005 | Solomon | |
| 2006/0004410 A1 | 1/2006 | Nobis et al. | |
| 2006/0009784 A1 | 1/2006 | Behl et al. | |
| 2006/0161040 A1 | 7/2006 | McCarthy et al. | |
| 2006/0178682 A1 | 8/2006 | Boehlke | |
| 2007/0010857 A1* | 1/2007 | Sugimoto et al. | 606/232 |
| 2007/0055303 A1 | 3/2007 | Vidlund et al. | |
| 2007/0083229 A1* | 4/2007 | Deutsch | 606/213 |
| 2007/0106310 A1 | 5/2007 | Goldin et al. | |
| 2008/0228165 A1* | 9/2008 | Spence et al. | 604/510 |
| 2008/0228265 A1* | 9/2008 | Spence et al. | 623/2.36 |
| 2008/0228267 A1* | 9/2008 | Spence et al. | 623/2.36 |
| 2009/0018655 A1 | 1/2009 | Brunelle et al. | |
| 2009/0076547 A1* | 3/2009 | Sugimoto et al. | 606/232 |

FOREIGN PATENT DOCUMENTS

| | | |
|---|---|---|
| WO | WO 2006105008 | 10/2006 |
| WO | WO 2008091391 | 7/2008 |

* cited by examiner

TISSUE PLICATION DEVICE AND METHOD FOR ITS USE

CROSS-REFERENCE TO RELATED APPLICATIONS

This application claims the benefit of U.S. Provisional Application Ser. No. 61/194,671 filed on Sep. 12, 2008, the disclosure of which is hereby incorporated by reference in its entirety.

BACKGROUND

Mitral regurgitation is an issue affecting millions of people worldwide. It is the backflow of blood from the left ventricle into the left atrium due to incomplete closure of the mitral valve. There are surgical options available that return the valve to a functional geometry, however, surgery presents many risks to the patient.

DESCRIPTION

This invention generally provides devices that can be deployed into the annulus of the mitral valve, and be acted upon to reduce the annular circumference and/or desirably change the functional geometry of the mitral valve. A reduction in annular circumference can, for example, reduce the septal lateral dimension of the valve enough to ensure that functional leaflet coaptation returns. These devices can be delivered percutaneously, thus eliminating the need for open heart surgery. At the physician's discretion, these devices can be delivered surgically, as well. The devices may also be used in other surgical procedures.

Figure 1:
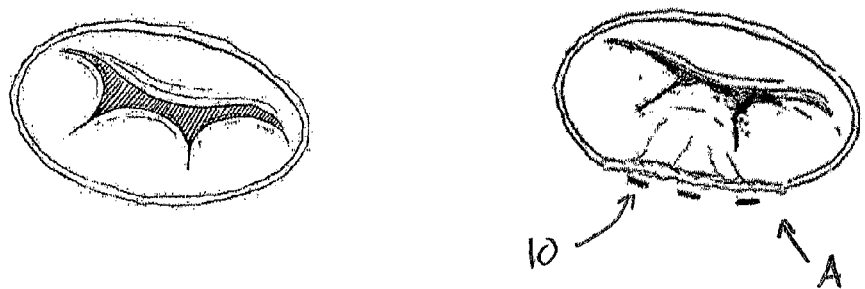
FIG. 1 is a perspective view of the mitral valve illustrated, respectively, in pretreatment and post treatment state.
Figure 2:
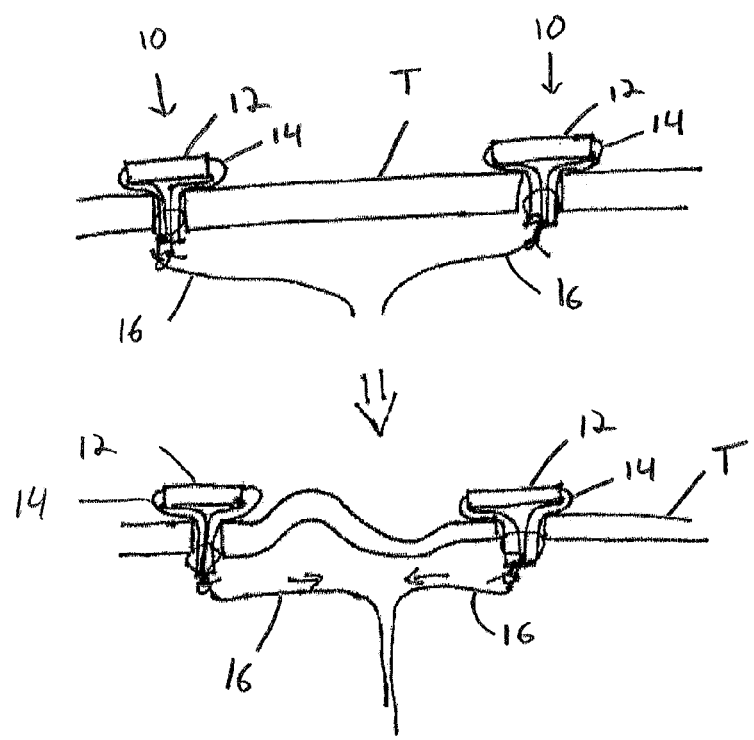
FIG. 2 is a schematic elevational view illustrating, respectively, the anchors in an untensioned and a tensioned state.

An illustrative embodiment of a method of the invention involves placing two or more tissue fixation devices, referred to as anchors 10, on or near the posterior region of the mitral valve annulus "A". Alternatively, the anchors 10 can be positioned on or near both the posterior and anterior regions, or at other locations of the heart. In one method, the anchors are tensioned together to reduce the distance between them (FIG. 1). This effectively pulls the posterior annulus in closer proximity to the anterior annulus of the mitral valve, reduces the septal lateral dimension, facilitates coaptation of the valve leaflets, and reduces or eliminates the mitral regurgitation (FIG. 2).

Figure 3:
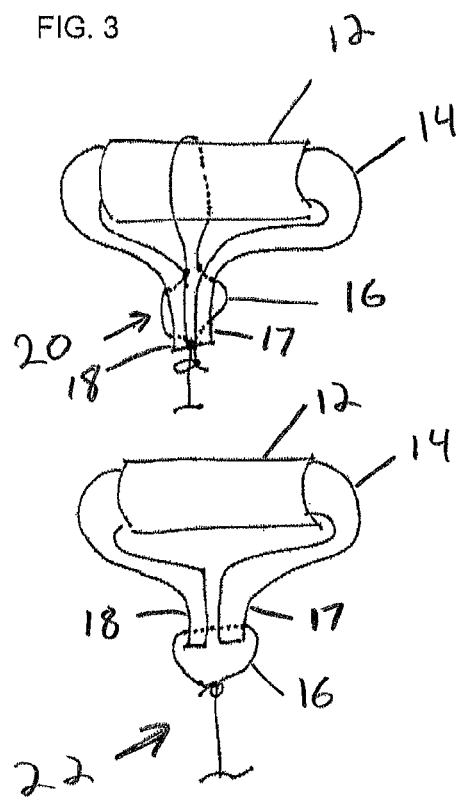
FIG. 3 is a schematic view showing examples of two suture patterns.

The specific anchor design is shown in FIG. 3 (Two examples of suture pattern 20, 22 are illustrated). It consists of a semi-rigid bar 12, ribbon of fabric 14 and a suture 16. The ribbon 14 has a first end 17 and a second end 18 and extends through the bar 12. In suture pattern 20, the suture 16 passes transversely through the first and second ends 17, 18 of the ribbon 14 and extends over the bar 12, while a tail end of the suture remains external to the ribbon 14. In suture pattern 22, the suture 16 passes transversley through the first and second ends 17, 18, of the ribbon 14, while a tail end of the suture remains external to the ribbon 14. As can be seen in FIG. 2, it is intended that the bar 12 portion is anchored on one side of the tissue "T" while the suture and fabric extend through the tissue. The sutures of two or more anchors are the means for tensioning the anchors together. A lock can be applied to the sutures in order to maintain the tension between the anchors.

Figure 4:
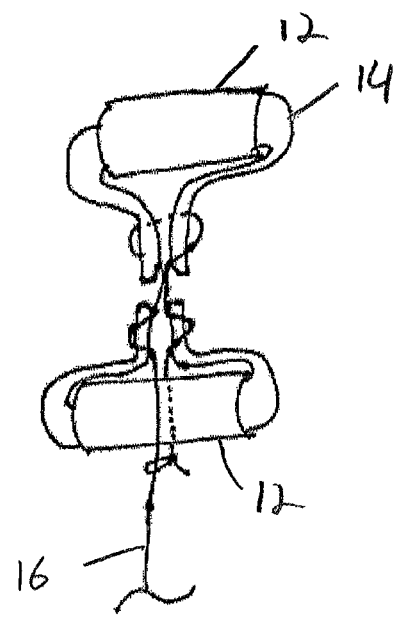
FIG. 4 is a schematic elevation view of an alternative anchor design.

In an alternative design (FIG. 4), the anchor could consist of two bars 12, located on opposing sides of a tissue structure. This configuration could serve to compress the tissue locally and increase the retention strength of the anchor. Like the previous description, the respective sutures of the anchors are the means for tensioning the anchors together.

The quantities and positions of these anchors can be adapted in response to anatomical and etiological variations. Examples of typical configurations of these anchors are: set of two anchors, two or more sets of two anchors, set of three anchors, along the posterior annulus, along the anterior annulus, along both the posterior and anterior annuli.

With respect to the components of the anchor 10, the bar 12 could exist in a number of cross-sections (e.g., cylindrical, rectangular, I-beam, annular, etc.) and materials (metals like platinum and its alloys, titanium, stainless steel, or polymers like polyester, polypropylene, or other materials that would provide the required functional properties and biocompatibility). The fabric 14 could also be a sheet, cord or other structure that would support the plication tensions of this tissue plication treatment and not damage the tissue. Materials such as polyester, polypropylene and polytetrafluoroethylene can be used to fabricate this ribbon. The suture 16 could be a monofilament or braided structure, a wire or other element that can connect and tension multiple anchors. Typical suture materials are polyester, polypropylene, silk, and stainless steel.

These anchors can be delivered to the mitral valve annulus through a delivery catheter with the anchor loaded inside the delivery catheter or mounted on the outside of the catheter. The mitral valve can be accessed with the catheter via transseptal technique or retrograde approach. The catheter may be used in combination with guide wires and/or guide catheters per standard catheter technique, and guided and/or imaged with traditional visualization tools, such as echocardiography and fluoroscopy.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for use in a tissue plication procedure comprising:
   an anchor that comprises:
      a reinforcing bar;
      a ribbon that passes through the bar, the ribbon having first and second ends such that the first and second ends extend from opposite ends of the bar;
      a suture having a first section that is external to the ribbon and a second section that extends transversely through at least the first and second ends of the ribbon at fixed locations thereof,
   and a second anchor comprising a second suture, so that when both the anchor and second anchor are implanted adjacent a valve annulus, valve tissue is plicated when tension is applied to the suture and second suture.

2. The device of claim 1, wherein the suture further extends over the bar.

3. The device of claim 1, wherein the first section comprises a tail section that depends downwardly from the second section and from the first and second ends of the ribbon.

4. The device of claim 1, wherein the second section extends transversely through the first and second ends of the ribbon proximate points at which the first and second ends of the ribbon terminate.

5. A method for treating mitral regurgitation, comprising:
  delivering at least two anchors to a position adjacent a mitral valve annulus of a heart, each anchor comprising:
    a reinforcing bar;
    a ribbon that passes through the bar, the ribbon having first and second ends such that the first and second ends extend from opposite ends of the bar;
    a suture having a first section that is external to the ribbon and a second section that extends transversely through at least the first and second ends of the ribbon at fixed locations thereof;
  deploying, at a first position, the at least one anchor into tissue adjacent the mitral valve annulus such that the bar is disposed on one side of the tissue, the ribbon extends at least partially through the tissue, and the suture extends from an opposite side of the tissue;
  deploying, at second position spaced from the first, a second anchor into tissue adjacent the mitral valve annulus such that the bar is disposed on one side of the tissue, the ribbon extends at least partially through the tissue, and the suture extends from an opposite side of the tissue;
  applying tension to each of the sutures of the two anchors to plicate the tissue.

6. The method of claim 5, wherein the step of applying tension comprises the step of applying tension to the first sections of the sutures that extend downwardly from the respective ribbons.

7. The method of claim 6, wherein the application of tension to the first sections of the sutures causes the anchors to be drawn together, thereby causing the tissue to be plicated.

8. The method of claim 5, wherein the first sections of the respective sutures lie below the opposite side of the tissue and are free so as to permit tension to be applied thereby to cause the respective bars on the one side of the tissue to be drawn together.

* * * * *